United States Patent
Il et al.

(10) Patent No.: US 9,835,551 B2
(45) Date of Patent: Dec. 5, 2017

(54) INFRARED GAS ANALYSIS DEVICE, AND METHOD FOR USING SAME

(71) Applicant: UBE INDUSTRIES, LTD., Ube-shi, Yamaguchi (JP)

(72) Inventors: Hirofumi Il, Ube (JP); Yuya Fukui, Ube (JP); Syuji Tanaka, Ube (JP)

(73) Assignee: UBE INDUSTRIES, LTD., Ube-shi (JP)

(*) Notice: Subject to any disclaimer, the term of this patent is extended or adjusted under 35 U.S.C. 154(b) by 0 days.

(21) Appl. No.: 15/321,372

(22) PCT Filed: Jul. 3, 2015

(86) PCT No.: PCT/JP2015/069263
§ 371 (c)(1),
(2) Date: Dec. 22, 2016

(87) PCT Pub. No.: WO2016/002928
PCT Pub. Date: Jan. 7, 2016

(65) Prior Publication Data
US 2017/0160191 A1     Jun. 8, 2017

(30) Foreign Application Priority Data
Jul. 4, 2014   (JP) .................................. 2014-138882

(51) Int. Cl.
*G01N 21/3504* (2014.01)
*G01N 33/00* (2006.01)

(52) U.S. Cl.
CPC ..... *G01N 21/3504* (2013.01); *G01N 33/0036* (2013.01); *G01N 2201/061* (2013.01)

(58) Field of Classification Search
CPC ........... G01N 21/3504; G01N 33/0036; G01N 2201/061
See application file for complete search history.

(56) References Cited

FOREIGN PATENT DOCUMENTS

| JP | S63-308540 A | 12/1988 |
|----|----|----|
| JP | H06-86063 U | 12/1994 |
| JP | H07-311154 A | 11/1995 |
| JP | 2011-033636 A | 2/2011 |
| JP | 2012-068164 A | 4/2012 |

OTHER PUBLICATIONS

Sep. 29, 2015 International Search Report issued in International Patent Application No. PCT/JP2015/069263.
Jan. 19, 2017 Written Opinion issued in International Patent Application No. PCT/JP2015/069263.

*Primary Examiner* — Mark R Gaworecki
(74) *Attorney, Agent, or Firm* — Oliff PLC (57) ABSTRACT

The infrared gas analysis device includes: a measurement cell to allow a sample gas containing a component to be measured to flow therethrough; a comparison cell including a reference gas; a pair of light sources provided in one end side of the measurement cell and the comparison cell, the cells being irradiated with an infrared ray from one and the other of the light sources, respectively; and a detection unit provided in another end side of the measurement cell and the comparison cell to detect the component to be measured by using infrared rays output from the measurement cell and the comparison cell. A gas for detection made of a component different from the component to be measured and having an infrared absorption band at at least a part of wavenumbers in infrared absorption bands of the component to be measured is encapsulated in the detection unit.

11 Claims, 7 Drawing Sheets

INFRARED GAS ANALYSIS DEVICE, AND METHOD FOR USING SAME

TECHNICAL FIELD

The present disclosure relates to an infrared gas analysis device, and a method for using the same.

BACKGROUND ART

A non-dispersive infrared absorption method is known, in which a sample gas is directly irradiated with an infrared ray from an infrared light source to measure the gas concentration of each component without dispersing the infrared ray into those of different wavenumbers. Gas analysis with a non-dispersive infrared absorption method provides quick measurement of various components contained in a gas. Thus, analysis with a non-dispersive infrared absorption method is used for various applications as an approach to directly measure components contained in a gas.

For an infrared gas analysis device used in such analysis, it is known that variation in output of a light source, a stain on a cell and window, etc., cause measurement error. To decrease measurement error, Patent Literature 1 suggests providing, in addition to a main detector in which a gas having sensitivity to the infrared absorption band of a gas to be measured is encapsulated, a compensating detector in which a gas not having sensitivity to the infrared absorption band of a gas to be measured is encapsulated. Such a device configuration provides zero-drift correction for improvement of measurement precision.

Influence of other interferential components is considered as another cause for measurement error of an infrared gas analysis device. Specifically, it is concerned that, in some sample gas compositions, the wavenumber of the infrared peak of a component contained in the sample gas overlaps with that of another component to lower the measurement precision for a component to be measured. For such a phenomenon, for example, Patent Literature 2 suggests a technique to decrease influence of a component different from a component to be measured by providing a detector for interferential components separately from a detector for a component to be measured and using a gas filter to absorb infrared rays in a specific wavenumber region.

CITATION LIST

Patent Literature

Patent Literature 1: Japanese Unexamined Utility Model Publication No. H6-86063
Patent Literature 2: Japanese Unexamined Patent Publication No. 2012-68164

SUMMARY OF INVENTION

Technical Problem

Infrared gas analysis devices can analyze various sample gases at a high precision, and are thus utilized, for example, for various production devices and research equipment. In some applications, subjects to be measured may be highly harmful components such as explosive components and toxic components. In such a case, it is required not only to thoroughly take safety measures by workers but also to take countermeasures such as automation of gas sampling and employment of explosion-proof equipment.

Typically, a gas consisting of a component to be measured is encapsulated in a detection unit to detect a component to be measured in an infrared gas analysis device. Thus, in the case that the component to be measured is highly harmful, loss of safety is expected. In the case that the concentration of an explosive gas such as methyl nitrite is measured, for example, high dangerousness is expected. For this reason, a technique to ensure sufficient safety even in the case that a component to be measured is highly harmful has been required to be established.

Accordingly, an object of the present invention is, in one aspect, to provide an infrared gas analysis device excellent in safety. In another aspect, an object of the present invention is to provide a method for using an infrared gas analysis device.

Solution to Problem

The present invention provides, in one aspect, an infrared gas analysis device comprising: a measurement cell to allow a sample gas containing a component to be measured to flow therethrough; a comparison cell including a reference gas; a pair of light sources provided in one end side of the measurement cell and the comparison cell, the measurement cell and the comparison cell being irradiated with an infrared ray from one and the other of the light sources, respectively; and a detection unit provided in another end side of the measurement cell and the comparison cell to detect the component to be measured by using infrared rays output from the measurement cell and the comparison cell, wherein a gas for detection consisting of a component different from the component to be measured and having an infrared absorption band at at least a part of wavenumbers in infrared absorption bands of the component to be measured is encapsulated in the detection unit.

The infrared gas analysis device comprises a detection unit to encapsulate a gas for detection consisting of a component different from the component to be measured. Accordingly, an infrared gas analysis device sufficiently excellent in safety can be provided even in the case that the component to be measured has harmfulness such as inflammability, explosiveness, and toxicity. In addition, even in the case that the component to be measured is easily decomposable, lowering of measurement precision can be suppressed to provide an infrared gas analysis device excellent in stability in measurement. The gas for detection has an infrared absorption band at at least a part of wavenumbers (wave lengths) in the infrared absorption bands of the component to be measured, and thus provides detection of the component to be measured at a sufficient precision. Here, "at least a part of wavenumbers (wave lengths) in the infrared absorption bands" encompasses "all wavenumbers (wave lengths) in the infrared absorption bands".

The inner space of the detection unit to encapsulate the gas for detection may be separated into a first chamber in the side of the measurement cell and a second chamber in the side of the comparison cell. Further, the detection unit may be configured to detect the component to be measured on the basis of temperature difference between the first chamber and the second chamber. This enables detection of the component to be measured at a high precision in a simple structure.

In the infrared gas analysis device in some embodiments, the component to be measured is a nitrite ester, and the gas for detection may contain ammonia. This enables detection of the component to be measured in safety even in the case that the component to be measured is a highly explosive component such as a nitrite ester. The infrared gas analysis device may be for online analysis for a production device for a nitrite ester. Since ammonia is less explosive than nitrite esters, use of ammonia for the gas for detection can enhance the safety of the infrared gas analysis device.

The present invention provides, in another aspect, a method for using an infrared gas analysis device, the infrared gas analysis device comprising: a measurement cell to allow a sample gas containing a component to be measured to flow therethrough; a comparison cell including a reference gas; a pair of light sources provided in one end side of the measurement cell and the comparison cell, the measurement cell and the comparison cell being irradiated with an infrared ray from one and the other light sources, respectively; and a detection unit provided in another end side of the measurement cell and the comparison cell, and the method comprising: a step of irradiating the measurement cell and the comparison cell with an infrared ray from the light sources while the sample gas is allowed to flow through the measurement cell; and a step of detecting the component to be measured on the basis of temperature change of a gas for detection encapsulated in the detection unit and consisting of a component different from the component to be measured, wherein the temperature change is caused by infrared rays entering the detection unit from the measurement cell and the comparison cell, and the gas for detection has an infrared absorption band at at least a part of wavenumbers in infrared absorption bands of the component to be measured.

The method for using an infrared gas analysis device comprises a step of detecting the concentration of the component to be measured on the basis of temperature change of a gas for detection encapsulated in the detection unit and consisting of a component different from the component to be measured. Thus, even in the case that the component to be measured is highly harmful, the infrared gas analysis device can be used in excellent safety by using a gas less harmful than the component to be measured for the gas for detection. Further, lowering of measurement precision can be suppressed to enhance the stability of measurement even in the case that the component to be measured is easily decomposable. Furthermore, the gas for detection has an infrared absorption band at at least a part of wavenumbers in infrared absorption bands of the component to be measured, and thus the component to be measured can be detected at a sufficient precision.

Advantageous Effects of Invention

The present invention can provide, in one aspect, an infrared gas analysis device excellent in safety. Further, the present invention can provide, in another aspect, a method for using an infrared gas analysis device excellent in safety.

DESCRIPTION OF EMBODIMENTS

Now, some embodiments of the present invention will be described occasionally with reference to drawings. However, these embodiments in the following are examples to describe the present invention, and are not intended to limit the present invention to the following contents. In the following description, an identical sign is used for identical elements or elements having an identical function, and redundant descriptions will be occasionally omitted. Positional relation such as up and down and left and right is based on positional relation as shown in a drawing unless otherwise specified. In addition, the dimensional ratio of a drawing is not limited to the ratio as illustrated.

Figure 1:
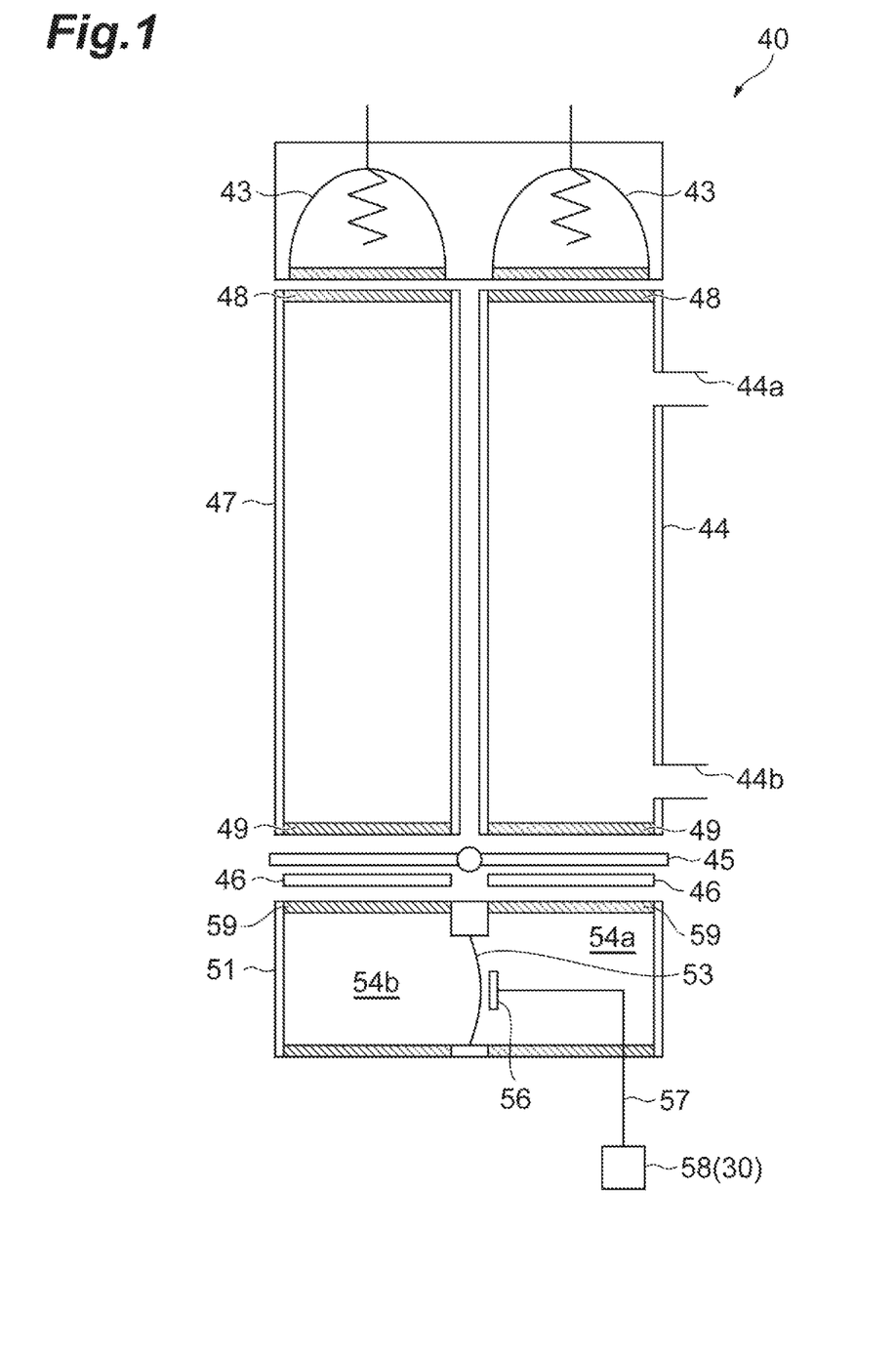
FIG. 1 illustrates one embodiment of the infrared gas analysis device.

FIG. 1 illustrates one embodiment of the infrared gas analysis device. An infrared gas analysis device 40 in FIG. 1 is an analysis device to quantify a component to be measured contained in a sample gas with a non-dispersive infrared absorption method (NDIR).

The infrared gas analysis device 40 comprises: a measurement cell 44 to allow a sample gas containing a component to be measured to flow therethrough; a comparison cell 47 including a reference gas; a pair of light sources 43, 43 provided in one end side of the measurement cell 44 and the comparison cell 47, the measurement cell 44 and the comparison cell 47 being irradiated with an infrared ray from one and the other of the light sources 43, 43, respectively; and a detection unit 51 provided in another end side of the measurement cell 44 and the comparison cell 47 to detect the concentration of the component to be measured by using infrared rays output from the measurement cell 44 and the comparison cell 47.

The measurement cell 44 and the comparison cell 47 are provided to lie next to each other. Examples of the reference gas encapsulated in the comparison cell 47 include inert gases such as nitrogen gas and argon gas. At one end of each of the measurement cell 44 and the comparison cell 47, a transmission window 48 to allow an infrared ray from a light source 43 to transmit therethrough is provided. The measurement cell 44 and the comparison cell 47 are disposed in such a way that the transmission windows 48 of them are positioned opposite to the light sources 43, 43. Examples of the material of the transmission window 48 include $CaF_2$, $Al_2O_3$, and $BaF_2$.

At another end of each of the measurement cell 44 and the comparison cell 47, a transmission window 49 to allow an infrared ray after passing through the measurement cell 44 or the comparison cell 47 to transmit therethrough is provided. In addition, transmission windows 59 are provided in the side of the measurement cell 44 and the comparison cell 47 of the detection unit 51. Examples of the material of the transmission windows 49, 59 include $CaF_2$, $Al_2O_3$, and $BaF_2$. An infrared ray after passing through each of the measurement cell 44 and the comparison cell 47 is output from the transmission window 49 and enters the detection unit 51 from the transmission window 59 of the detection unit 51 disposed opposite to the transmission window 49. Between the transmission window 49 and the detection unit 51, a light chopper 45 and an optical filter 46 are provided. The light chopper 45 allows an infrared ray output from the transmission window 49 to intermittently enter the detection unit 51.

The optical filter 46 absorbs an infrared ray within a specific wavenumber range. The optical filter 46 is selected so that an infrared ray with wavenumbers at which both of the infrared absorption band of the component to be measured and the infrared absorption band of a gas for detection are detected enters the detection unit 51. This allows an infrared ray of wavenumbers including at least a part of wavenumbers in the infrared absorption bands of the component to be measured and at least a part of wavenumbers in the infrared absorption bands of a gas for detection to enter the detection unit 51. In other words, the component to be measured and a gas for detection both have an infrared absorption band within the wavenumber range of an infrared ray entering the detection unit 51. Here, an infrared absorption band refers to a wavenumber range an infrared ray of which is absorbed.

The detection unit 51 is, for example, a capacitor microphone detector. The detection unit 51 encapsulates a gas for detection consisting of a component different from the component to be measured. The inner space of the detection unit 51 to encapsulate the gas for detection is separated into a first chamber 54a in the side of the measurement cell 44 and a second chamber 54b in the side of the comparison cell 47 by a thin membrane 53 provided near the center portion. Thus, the first chamber 54a and the second chamber 54b are formed in the detection unit 51. The first chamber 54a and the second chamber 54b are filled with an identical gas for detection.

The light source 43, the measurement cell 44, and the first chamber 54a in one side are disposed in series in the order presented. In parallel with this, the light source 43, the comparison cell 47, and the second chamber 54b in another side are disposed in series in the order presented. The detection unit 51 is configured to detect the component to be measured on the basis of temperature difference between the first chamber 54a and the second chamber 54b.

For the thin membrane 53, an insulating polymer film of a polyimide or the like on which an electroconductive film of a metal is formed through sputtering can be used. Into the first chamber 54a, an infrared ray after passing through the measurement cell 44 enters. Into the second chamber 54b, an infrared ray after passing through the comparison cell 47 enters.

In the first chamber 54a, a fixed electrode 56 is disposed opposite to the electroconductive film of the thin membrane 53. To the fixed electrode 56, a lead 57 is connected. The lead 57 is connected to a signal processing unit 58. When a difference arises between the temperature of the gas for detection in the first chamber 54a and the temperature of the gas for detection in the second chamber 54b, the distance between the fixed electrode 56 and the thin membrane 53 changes. As a result, an electrical signal is output to the signal processing unit 58. By processing this electrical signal with the signal processing unit 58, the presence or absence of the component to be measured or the concentration of the component to be measured can be determined.

The component to be measured contained in a sample gas flowing through the measurement cell 44 is not particularly limited as long as it has an infrared absorption peak, and examples thereof include various components such as CO, $NO_x$, $SO_x$, hydrocarbons, alcohols, and nitrite esters. The detection unit 51 in the infrared gas analysis device 40 encapsulates a gas for detection consisting of a component different from the component to be measured. The gas for detection has an absorption peak in the infrared absorption bands of the component to be measured. In other words, the infrared absorption peak of the component to be measured and the absorption peak of the gas for detection overlap at at least a part of the wavenumbers. Accordingly, quantitative analysis or qualitative analysis for the component to be measured can be carried out in high safety while the measurement precision is maintained, even in the case that the component to be measured is a harmful component.

Examples of harmful components to be measured include materials corresponding to hazardous materials under Fire Service Act and materials designated as poisonous substances under Poisonous and Deleterious Substances Control Act. Examples of highly harmful components to be measured include nitrite esters such as alkyl nitrites. Examples of the nitrite esters include methyl nitrite, ethyl nitrite, propyl nitrite, isopropyl nitrite, butyl nitrite, pentyl nitrite, hexyl nitrite, heptyl nitrite, octyl nitrite, and nonyl nitrite.

On the other hand, the gas for detection is less harmful than the component to be measured. An indicator of harmfulness is, for example, a lower limit of explosion limit (lower explosion limit) higher than that of the gas for detection. Use of a gas for detection having a lower limit value of explosion limit in the air higher than that of the component to be measured can reduce dangerousness when the gas for detection leaks in the worst case.

Figure 2:
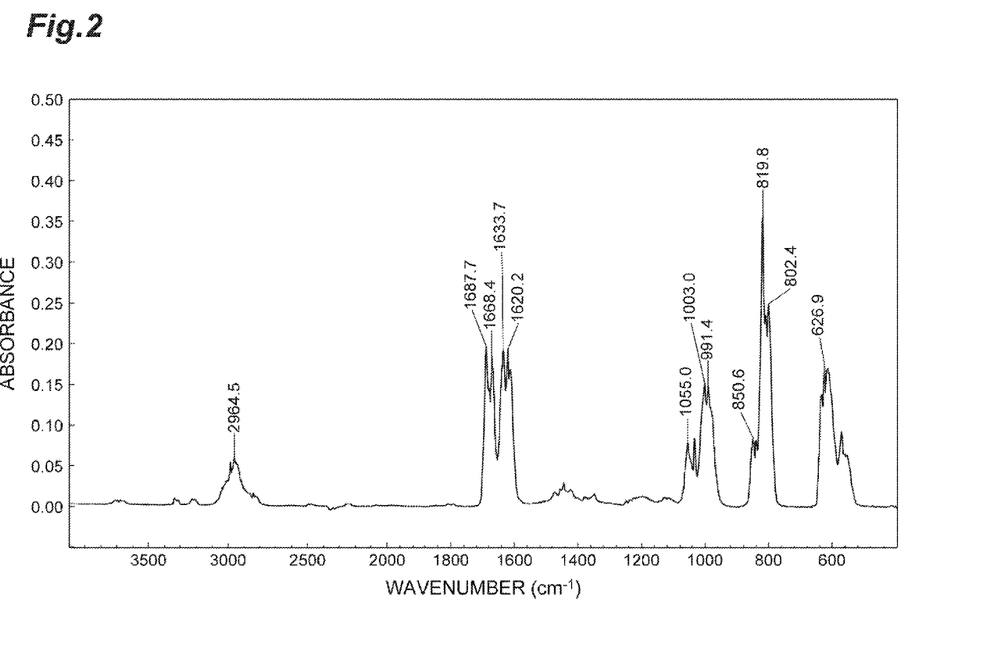
FIG. 2 is an infrared absorption spectrum of a nitrite ester.

In the case that the component to be measured is methyl nitrite, a gas containing ammonia can be used for the gas for detection. For example, a gas obtained by diluting ammonia with an inert gas can be used as the gas for detection. FIG. 2 is an absorption spectrum of methyl nitrite. As can be seen from FIG. 2, methyl nitrite has, for example, infrared absorption bands including absorption peaks due to N—O stretching vibration, etc. Methyl nitrite has infrared absorption bands including absorption peaks around 800 $cm^{-1}$, around 1000 $cm^{-1}$, and around 1670 $cm^{-1}$.

Figure 3:
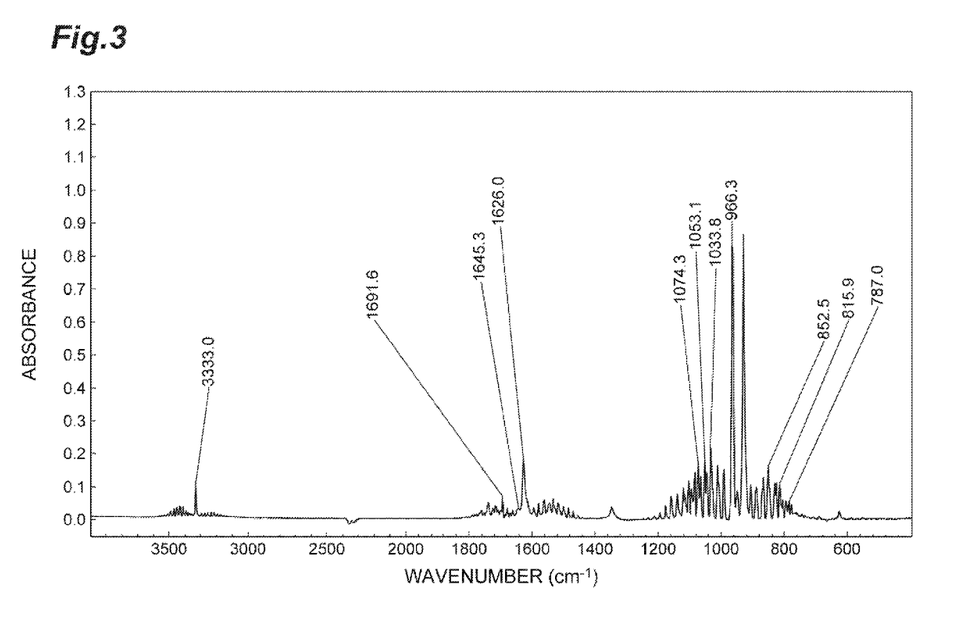
FIG. 3 is an infrared absorption spectrum of ammonia.

FIG. 3 is an infrared absorption spectrum of ammonia. As can be seen from FIG. 3, ammonia has infrared absorption bands including absorption peaks around 800 $cm^{-1}$, around 960 $cm^{-1}$, around 1040 $cm^{-1}$, and around 1650 $cm^{-1}$. Thus, ammonia has infrared absorption bands at at least a part of the infrared absorption bands of methyl nitrite. The component to be measured can be detected by allowing an infrared ray of a wavenumber range in which the absorption peak of methyl nitrite and the absorption peak of ammonia overlap to enter the detection unit 51. Examples of such wavenumber ranges include 780 to 860 $cm^{-1}$, 940 to 1080 $cm^{-1}$, and 1650 to 1700 $cm^{-1}$. Thus, quantitative analysis for methyl nitrite in a sample gas can be carried out without largely lowering the measurement precision even when ammonia is used for the gas for detection in place of methyl nitrite. Here, the wavenumber range of 940 to 1080 $cm^{-1}$ roughly corresponds to a wave length range of 926 to 1064 nm. The wavenumber range of 780 to 860 $cm^{-1}$ roughly corresponds to a wave length range of 1163 to 1282 nm. The wavenumber range of 1650 to 1700 $cm^{-1}$ roughly corresponds to a wave length range of 588 to 606 nm.

Use of ammonia, which has a lower limit of explosion limit higher than that of methyl nitrite as the component to be measured, for the gas for detection can enhance the safety of the infrared gas analysis device 40. The lower limit of explosion limit can be measured with a commercially available explosive range-measuring apparatus (e.g., explosion limit tester, manufactured by Kayaku Japan Co., Ltd.).

A method for measuring the concentration of the component to be measured with the infrared gas analysis device 40 will be described. A sample gas containing the component to be measured and not containing a component contained in the gas for detection is introduced into the measurement cell 44 from a gas inlet 44a provided in one end side of the measurement cell 44. The sample gas moves in the measurement cell 44 from the upper side to the lower side in FIG. 1, and is discharged from a gas outlet 44b provided in another end side of the measurement cell 44. In the measurement cell 44, the component to be measured contained in the sample gas absorbs an infrared ray of a predetermined wavenumber range (L1) among infrared rays which have entered the measurement cell 44 from the light source 43. Thereafter, infrared rays including the infrared ray of the wavenumber range (L1) passes through the light chopper 45 and the optical filter 46 to enter the first chamber 54a of the detection unit 51. Then, the gas for detection encapsulated in the first chamber 54a absorbs the infrared ray of the predetermined wavenumber and the temperature is elevated. The temperature elevation is designated as $\Delta T1$.

On the other hand, the reference gas contained in the comparison cell 47 has no absorption peaks in any of the wavenumber regions of the absorption peaks (infrared absorption bands) of the component to be measured. Thus, infrared rays entering from the light source 43 do not lose the infrared ray of the wavenumber range (L1) through absorption, and the infrared rays including the infrared ray of the wavenumber range (L1) enter the second chamber 54b of the detection unit 51. Then, the gas for detection encapsulated in the second chamber 54b absorbs the infrared rays including the infrared ray of the wavenumber range (L1) and the temperature is elevated. The temperature elevation is designated as $\Delta T2$. Infrared rays without the infrared ray of the wavenumber range (L1) absorbed in passing through the comparison cell 47 enter the second chamber 54b. Accordingly, the temperature elevation of the gas for detection encapsulated in the second chamber 54b, $\Delta T2$, is higher than the temperature elevation of the gas for detection encapsulated in the first chamber 54a, $\Delta T1$. That is, the relation of $\Delta T1 < \Delta T2$ is satisfied.

This temperature difference ($\Delta T2 - \Delta T1$) changes the distance between the fixed electrode 56 and the thin membrane 53, and an electrical signal is transmitted from the fixed electrode 56. This signal is input into the signal processing unit 58 via the lead 57. The signal processing unit 58 is a unit to output the concentration of the component to be measured on the basis of an electrical signal, and can include, for example, an amplifier, an arithmetic circuit, a CPU (Central Processing Unit), a ROM (Read Only Memory), a RAM (Random Access Memory), and an input/output interface. For example, a function to output the concentration of the component to be measured in accordance with an electrical signal is stored in the signal processing unit 58. A data table may be stored in place of a function. This enables the signal processing unit 58 to automatically output the concentration of the component to be measured.

In some other embodiments, after the concentration of the gas for detection is output from the signal processing unit 58, the concentration may be corrected with another computer or the like to calculate the concentration of the component to be measured. Specifically, it is as follows: in the case that the signal processing unit 58 is configured under the assumption that the component to be measured contained in a sample gas is identical to the component encapsulated in the detection unit 51, a measurement output from the signal processing unit 58 is an output as the concentration of the gas for detection; and thus, the concentration of the component to be measured can be determined by correcting the concentration of the component output from the signal processing unit 58.

In the case that the component to be measured is a nitrite ester and the gas for detection is ammonia, calculation to convert the concentration of ammonia calculated from the amount of energy absorption detected for the nitrite ester to the concentration of the nitrite ester can be conducted as follows.

For example, the ratio of the amount of energy absorption (i.e., an integrated value around peaks in the absorption spectrum) of a predetermined concentration of a nitrite ester to that of the equivalent concentration of ammonia within a predetermined wavenumber range (L1) is calculated as a coefficient in advance. Then, a measurement as the concentration of ammonia, due to that the gas for detection is ammonia, is multiplied by the coefficient to convert to the concentration of the nitrite ester. By storing the coefficient as a function in the signal processing unit 58 or a computer provided separately from the signal processing unit 58, the concentration of ammonia can be converted to the concentration of the nitrite ester.

Since the detection unit 51 can encapsulate a gas for detection different from the component to be measured, the safety can be sufficiently enhanced in the infrared gas analysis device 40. Accordingly, it is suitably used for online analysis for various production devices or experimental devices.

Further, in some other embodiments, the infrared gas analysis device 40 may include a control unit 30 in place of the signal processing unit 58. The control unit 30 has a function to output the concentration of the component to be measured on the basis of an electrical signal generated by the change of the distance between the fixed electrode 56 and the thin membrane 53 and a function to perform operation control for a production device or an experimental device on the basis of the concentration of the component to be measured output. In other words, the control unit 30 has the function of the signal processing unit 58 and a function to perform operation control for a production device or an experimental device in combination.

Figure 4:
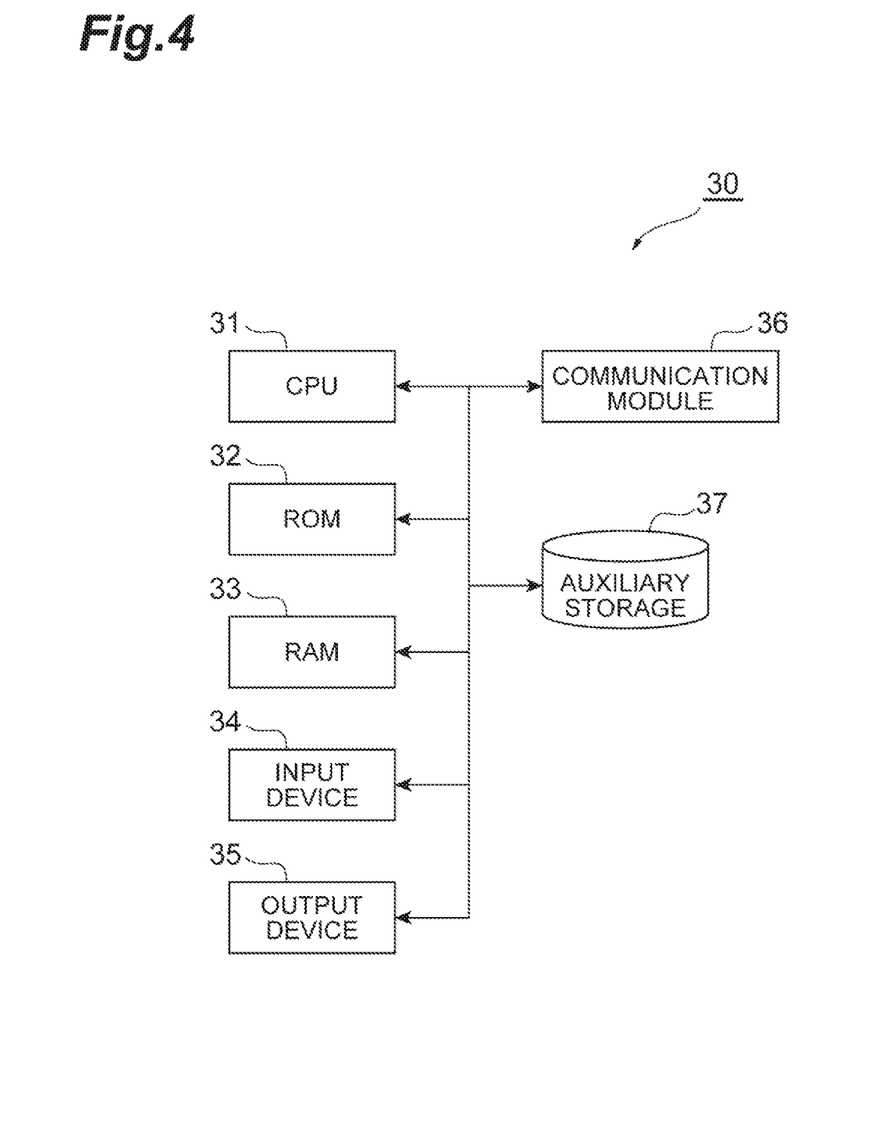
FIG. 4 is a hardware configuration diagram of a control unit.

FIG. 4 is a hardware configuration diagram of the control unit 30. As shown in FIG. 4, the control unit 30 can be physically configured as a common computer system including a CPU 31, a main memory such as a ROM 32 and a RAM 33, an input device 34 such as a keyboard and a mouse, an output device 35 such as a display, a communication module 36 such as a network card to send/receive data to/from another part in a production device or an experimental device, and an auxiliary storage 37 such as a hard disk.

Signal processing and control functions of the control unit 30 are achieved by reading a predetermined computer software into a hardware such as the CPU 31, the ROM 32, and the RAM 33 so as to operate the input device 34, the output device 35, and the communication module 36 and reading and writing data from/in the ROM 32, the RAM 33, and the auxiliary storage 37 under control of the CPU 31. The ROM 32, the RAM 33, or the auxiliary storage 37 may store data and a function to calculate the concentration of the component to be measured from an electrical signal input via the lead 57.

Figure 5:
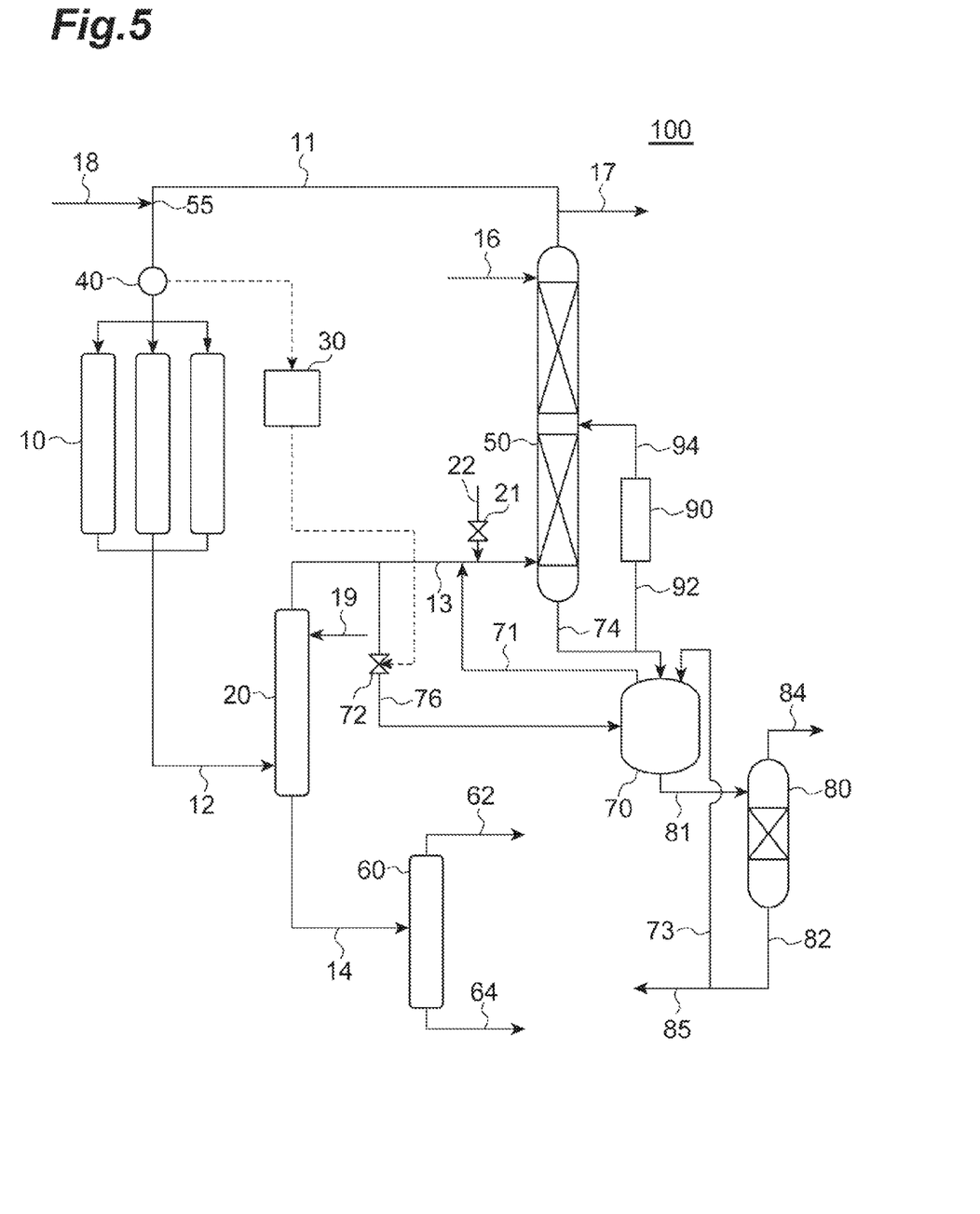
FIG. 5 illustrates an example of the infrared gas analysis device used as an online analysis device.

FIG. 5 illustrates an example of the infrared gas analysis device 40 used as an online analysis device. A production device 100 illustrated in FIG. 5 is a production device for a carbonate ester. The production device 100 includes a first reactor 10, which has a catalyst to allow carbon monoxide and a nitrite ester to react together to produce a carbonate ester and nitric oxide and produces a second gas containing a carbonate ester and nitric oxide from a first gas containing carbon monoxide, a nitrite ester, and nitric oxide.

The production device 100 further includes: an absorption column 20 to allow the second gas obtained in the first reactor 10 to contact with an absorbing solution to absorb a carbonate ester to separate into a condensate containing a carbonate ester and a noncondensable gas containing nitric oxide; a second reactor 50 to introduce a mixed gas of the noncondensable gas and oxygen gas and an alcohol and allow nitric oxide, oxygen, and an alcohol to react together to produce a third gas containing a nitrite ester and nitric oxide; and a junction part 55 to allow the third gas and carbon monoxide to join together to obtain the first gas.

In the first reactor 10, a gas phase reaction represented by the following formula (1) proceeds. In the formula (1), R denotes an alkyl group.

$$CO + 2RONO \rightarrow ROC(=O)OR + 2NO \qquad (1)$$

The second gas introduced to the lower part of the absorption column 20 from the first reactor 10 through a passage 12 is brought into countercurrent contact with an absorbing solution for absorption of a carbonate ester (hereinafter, simply referred to as "absorbing solution") introduced from a passage 19 connected to the upper part of the absorption column 20. In this way, the second gas and the absorbing solution are brought into gas-liquid contact to allow at least a part of the carbonate ester contained in the second gas to be absorbed in the absorbing solution. As a result, a condensate containing a carbonate ester and the absorbing solution and a noncondensable gas containing nitric oxide are obtained.

The condensate containing the absorbing solution and a carbonate ester, which is obtained in the absorption column 20, is extracted from a passage 14 linked to the bottom of the absorption column 20. The condensate passes through the passage 14 to be introduced into a distillation column 60. In the distillation column 60, the condensate is separated into the absorbing solution and a carbonate ester by difference in boiling point. In the case that an alcohol with low boiling point such as methanol and ethanol is used for the absorbing solution, the alcohol is discharged from a passage 62 linked to the top of the distillation column 60 and a carbonate ester is discharged from a passage 64 linked to the bottom of the distillation column 60.

The noncondensable gas containing nitric oxide and obtained in the absorption column 20 is extracted from a passage 13 linked to the upper part of the absorption column 20 and flows through the passage 13 to the second reactor 50. The noncondensable gas may contain carbon monoxide. To the passage 13, a passage 76 to feed the noncondensable gas to a third reactor 70 and a passage 22 to introduce oxygen gas are linked in the order presented from the upstream side. The amount of introduction of oxygen gas is adjusted with a flow regulating valve 21.

The oxygen gas fed from the passage 22 is mixed with the noncondensable gas to form a mixed gas. The mixed gas containing the noncondensable gas and oxygen gas passes through the passage 13 to be introduced into the second reactor 50. The mixed gas after passing through the passage 13 is introduced into the second reactor 50 from the lower side, and then brought into countercurrent contact with an alcohol (ROH) introduced from a passage 16 linked to the upper side of the second reactor 50. As a result, a nitrite ester (RONO) and water are generated.

A part or all of the bottom liquid in the second reactor 50 may pass through a passage 92 linked to a passage 74, a cooler 90, and a passage 94 in the order presented to return to the second reactor 50. This enables easy control of the reaction temperature in the second reactor 50. The temperature in the second reactor 50 may be 10 to 60° C.

The third gas extracted from the upper part of the second reactor 50 contains nitric oxide and trace components such as nitrous oxide and carbon dioxide in addition to a nitrite ester. These trace components can be appropriately discharged to the outside of the system as an off-gas through a passage 17 branching from a passage 11. The third gas flows through the passage 11 to the junction part 55. At the junction part 55, CO is fed through a passage 18.

The first gas obtained in the junction part 55 is fed to the first reactor 10. In this way, the production device 100 allows nitrogen components to circulate while continuously feeding CO as a raw material to continuously produce a carbonate ester as an intended product. Nitrogen components such as NO and a nitrite ester are reused while circulating in the production device 100. In the bottom liquid discharged from the bottom of the second reactor 50, nitric acid, an alcohol, etc., are contained in addition to water. In view of this, the production device 100 includes the third reactor 70 to produce a nitrite ester from the bottom liquid containing water, nitric acid, and an alcohol and fed from the bottom of the second reactor 50, and the noncondensable gas.

From the upper part of the third reactor 70, a fourth gas containing a nitrite ester is discharged. The fourth gas flows through a passage 71 and joins the noncondensable gas flowing through the passage 13, and is then fed to the second reactor 50. To the bottom of the third reactor 70, a passage 81 for extraction of the reaction solution is connected. The reaction solution containing water, an alcohol, nitric acid, etc., which is obtained in the third reactor 70, flows through the passage 81 to be fed to a nitric acid-concentrating column 80.

In the nitric acid-concentrating column 80, the reaction solution is heated. From a passage 84 connected to the top of the nitric acid-concentrating column 80, a part or all of water and an alcohol is obtained as a distillate. From a passage 82 connected to the bottom of the nitric acid-concentrating column 80, a concentrate of concentrated nitric acid is obtained. A part of the concentrate concentrated in the nitric acid-concentrating column 80 flows through the passage 82 and a passage 73 connected to the passage 82 to be fed to the third reactor 70. A part of the concentrate may be allowed to flow through a passage 85 to be discharged as an effluent.

To the passage 11 through which the first gas flows, the infrared gas analysis device 40 is connected. Specifically, the gas inlet 44a and the gas outlet 44b are each connected to the passage 11 with a piping or the like. This allows a part of the first gas flowing through the passage 11 to be introduced into the measurement cell 44 through the gas inlet 44a. The first gas after flowing through the measurement cell 44 returns to the passage 11 through the gas outlet 44b.

The production device 100 includes: the infrared gas analysis device 40 to measure the concentration of the nitrite ester in the first gas; the flow rate-adjusting unit 72 to adjust the amount of the noncondensable gas to feed to the third reactor 70; and a control unit 30 configured to determine whether adjustment with the flow rate-adjusting unit 72 is needed on the basis of an analysis result of the infrared gas analysis device 40 and adjust the flow rate of the noncondensable gas with the flow rate-adjusting unit 72, as necessary. The control unit 30 has, for example, the configuration as illustrated in FIG. 4.

The carbonate ester produced with the production device 100 is, for example, a dialkyl carbonate. The two alkyl groups in a dialkyl carbonate molecule may be identical or different. Examples of the dialkyl carbonate include dimethyl carbonate, diethyl carbonate, dipropyl carbonate, diisopropyl carbonate, dibutyl carbonate, dipentyl carbonate, dihexyl carbonate, diheptyl carbonate, dioctyl carbonate, dinonyl carbonate, ethyl methyl carbonate, and ethyl propyl carbonate.

In the infrared gas analysis device 40, ammonia is encapsulated in the detection unit 51. This enables quick measurement of the concentration of a nitrite ester at a high precision concomitantly with sufficient enhancement of safety. Thus, production of a nitrite ester with the production device 100 can be stably continued.

Figure 6:
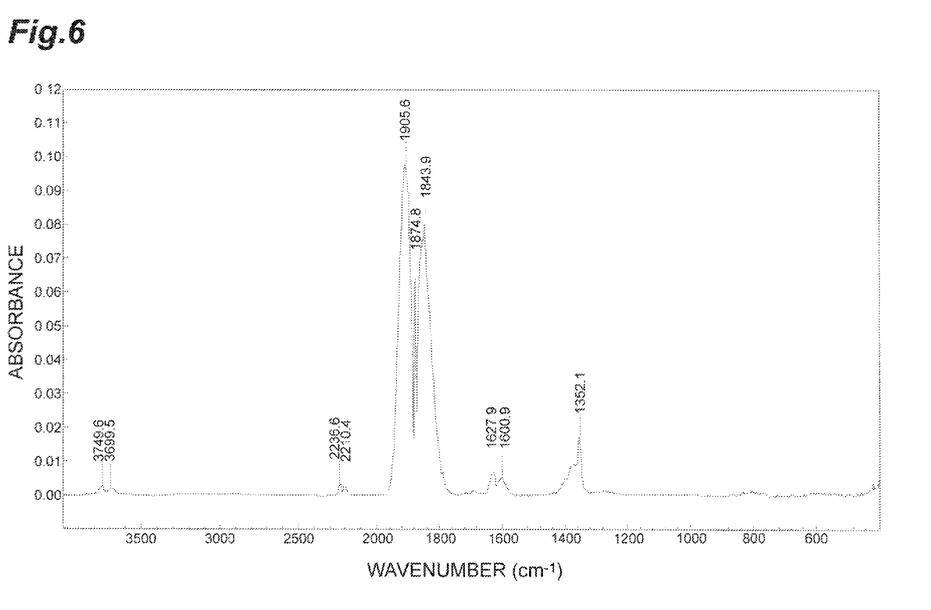
FIG. 6 is an infrared absorption spectrum of nitric oxide.
Figure 7:
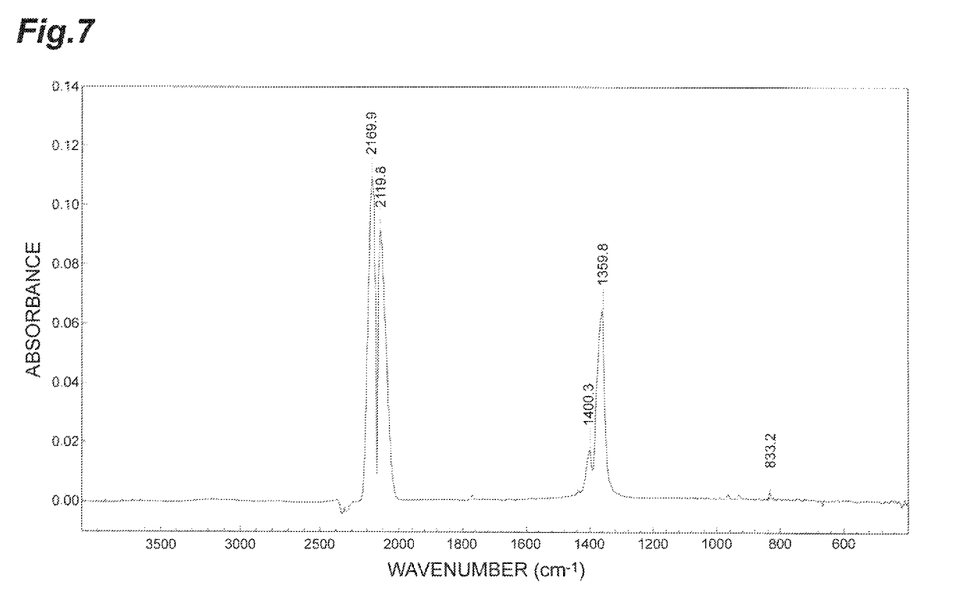
FIG. 7 is an infrared absorption spectrum of carbon monoxide.

FIG. 6 is an infrared absorption spectrum of nitric oxide. FIG. 7 is an infrared absorption spectrum of carbon monoxide. Nitric oxide and carbon monoxide each have very few absorption peaks, for example, around 780 to 860 cm$^{-1}$, 940 to 1080 cm$^{-1}$, and 1650 to 1700 cm$^{-1}$ among the wavenumber ranges of absorption peaks of a nitrite ester. Accordingly, even though the first gas contains nitric oxide and carbon monoxide, the concentration of methyl nitrite in the first gas can be measured at a high precision through appropriate selection of the wavenumber range of an infrared ray for measurement.

The infrared gas analysis device is not limited to the above-described mode. For example, the detection unit 51 may be a flow sensor detection unit to measure concentration by detecting movement of a gas for detection (e.g., ammonia) which occurs in accordance with the change of the amount of an infrared ray. Alternatively, a compensating detector may be provided separately from the detection unit 51 between the measurement cell 44 and the comparison cell 47 and the detection unit 51, or in the side opposite to the measurement cell 44 and the comparison cell 47 in the detection unit 51. For such a compensating detector, a compensating detector encapsulating a gas having no absorption peaks in the infrared absorption bands of the component to be measured can be used. By using a compensating detector and, for example, performing zero-drift correction, the concentration of the component to be measured can be measured at a sufficiently high precision for a long period. In addition to the zero-drift correction, span correction can be performed by using a nitrite ester with a known concentration.

Applications of the infrared gas analysis device 40 are not limited to the above-described application. For example, the production device 100 may be a production device for oxalic esters such as dialkyl oxalates and diaryl oxalates. In such a device, a nitrite ester circulates in the device, and thus the infrared gas analysis device 40 can be used as an online analysis device.

Among nitrite esters, ethyl nitrite is used for, for example, (i) a carbonylating agent for carbon monoxide, (ii) an oxidative carbonylating agent for olefins, or (iii) an acetalizing agent for olefins. The infrared gas analysis device 40 can be used for a production device and an experimental device utilizing such reactions. Examples of the reaction of (i) and (ii) include a reaction to produce dimethyl succinate from ethylene, carbon monoxide, and methyl nitrite, as shown in the following formula (2).

[Chemical Formula 1]

(2)

-continued

Another example of the reaction of (i) is a reaction to produce dimethyl malonate from ethenone, carbon monoxide, and methyl nitrite.

[Chemical Formula 2]

(3)

Examples of the reaction of (iii) include a reaction to produce 2,2-dimethoxypropane from propylene and methyl nitrite, as shown in the following formula (4).

[Chemical Formula 3]

(4)

The nitrite ester used for the above-mentioned reactions has high explosiveness. Accordingly, the infrared gas analysis device 40 can be suitably used for a production device or an experimental device to which such reactions are applied.

The method for using the infrared gas analysis device 40 comprises: a step of irradiating the measurement cell 44 and the comparison cell 47 with an infrared ray from the light sources 43, 43 while the sample gas is allowed to flow through the measurement cell 44; and a step of detecting the concentration of the component to be measured on the basis of temperature change of a gas for detection encapsulated in the detection unit 51 and consisting of a component different from the component to be measured, wherein the temperature change is caused by infrared rays entering the detection unit 51 from the measurement cell 44 and the comparison cell 47.

In the method for use, a component different from the component to be measured contained in the sample gas flowing through the measurement cell 44 can be encapsulated in the detection unit 51, and thus quantitative analysis for the component to be measured can be carried out in sufficient safety even in the case that the component to be measured is highly harmful. By using a gas having an infrared absorption band at at least a part of wavenumbers in infrared absorption bands of the component to be measured for a gas for detection, quantitative analysis for the component to be measured can be carried out at a sufficient precision. The method for use can be implemented on the basis of the content of the description on the infrared gas analysis device 40.

Hereinbefore, some embodiments of the present invention have been described; however, it is needless to say that the present invention is never limited to the above-described embodiments. Although ammonia is referred as an example of a gas for detection in the above-described embodiments, for example, the gas for detection is not limited to ammonia. Various gases having an infrared absorption band at at least a part of wavenumbers in infrared absorption bands of the component to be measured may be used.

INDUSTRIAL APPLICABILITY

The present disclosure can provide an infrared gas analysis device excellent in safety. In addition, a method for using an infrared gas analysis device excellent in safety can be provided.

REFERENCE SIGNS LIST

10: first reactor, 20: absorption column, 30: control unit, 34: input device, 35: output device, 36: communication module, 37: auxiliary storage, 40: infrared gas analysis device, 43: light source, 44: measurement cell, 44a: gas inlet, 44b: gas outlet, 45: light chopper, 46: optical filter, 47: comparison cell, 48, 49, 59: transmission window, 50: second reactor, 51: detection unit, 53: thin membrane, 54a: first chamber, 54b: second chamber, 55: junction part, 56: fixed electrode, 57: lead, 58: signal processing unit, 70: third reactor, 72: flow rate-adjusting unit, 100: production device

The invention claimed is:

1. An infrared gas analysis device comprising:
   a measurement cell to allow a sample gas containing a component to be measured to flow therethrough;
   a comparison cell including a reference gas;
   a pair of light sources provided in one end side of the measurement cell and the comparison cell, the measurement cell and the comparison cell being irradiated with an infrared ray from one and the other of the light sources, respectively; and
   a detection unit provided in another end side of the measurement cell and the comparison cell to detect the component to be measured by using infrared rays output from the measurement cell and the comparison cell, wherein
   the detection unit encapsulating a gas for detection consisting of a component, which is different from the component to be measured, having an infrared absorption band at least at a part of wavenumbers in infrared absorption bands of the component to be measured, and
   the detection unit comprises a first chamber, a second chamber, and a membrane separating the first chamber and the second chamber whereby the membrane is configured to move based on a temperature difference between the first chamber and second chamber.

2. The infrared gas analysis device according to claim 1, wherein
   an inner space of the detection unit to encapsulate the gas for detection is separated into the first chamber, which is in a side of the measurement cell, and the second chamber, which in a side of the comparison cell, and
   the detection unit detects the component to be measured on a basis of the temperature difference between the first chamber and the second chamber.

3. The infrared gas analysis device according to claim 2, wherein
   the component to be measured is a nitrite ester, and
   the gas for detection contains ammonia.

4. The infrared gas analysis device according to claim 3, for online analysis for a production device for a nitrite ester.

5. The infrared gas analysis device according to claim 2, wherein
   the detection unit has a signal processing unit and a computing unit,
   the signal processing unit outputs the concentration of the gas for detection on the basis of the temperature difference between the first chamber and the second chamber, and
   the computing unit calculates the concentration of the component to be measured by correcting the concentration of the gas for detection output from the signal for detection.

6. The infrared gas analysis device according to claim 2, wherein
   the membrane comprises an insulating polymer film on which an electro-conductive film of metal is formed.

7. The infrared gas analysis device according to claim 1, wherein
   the component to be measured is a nitrite ester, and
   the gas for detection contains ammonia.

8. The infrared gas analysis device according to claim 7, for online analysis for a production device for a nitrite ester.

9. A method for using an infrared gas analysis device, the method comprising:
   irradiating: (1) a measurement cell that allows a sample gas containing nitrite ester to be measured to flow therethrough, and (2) a comparison cell including a reference gas with an infrared ray from a pair of light sources provided in one end side of the measurement cell and the comparison cell while the sample gas is flowing through the measurement cell; and
   detecting the nitrite ester on a basis of temperature change of a gas including ammonia for detection encapsulated in a detection unit, which is provided in another end side of the measurement cell and the comparison cell, wherein
   the temperature change is caused by infrared rays entering the detection unit from the measurement cell and the comparison cell, and
   the gas for detection has an infrared absorption band at least at a part of wavenumbers in infrared absorption bands of the component to be measured.

10. The method according to claim 9, wherein
    the detection unit is separated in a first chamber and a second chamber by a membrane that is configured to move based on the temperature change between the first chamber and second chamber, and
    the detecting is performed by detecting that a membrane has moved because of the temperature change.

11. The method according to claim 10, wherein
    the membrane comprises an insulating polymer film on which an electro-conductive film of metal is formed.

* * * * *